(12) United States Patent
Harding

(10) Patent No.: US 7,935,318 B2
(45) Date of Patent: May 3, 2011

(54) MICROFLUIDIC CENTRIFUGATION SYSTEMS

(75) Inventor: Philip H. Harding, Albany, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 950 days.

(21) Appl. No.: 11/151,862

(22) Filed: Jun. 13, 2005

(65) Prior Publication Data

US 2006/0280653 A1    Dec. 14, 2006

(51) Int. Cl.
*B01L 3/00* (2006.01)

(52) U.S. Cl. ......... 422/502; 422/504; 422/506; 422/507

(58) Field of Classification Search ............ 422/50, 422/68.1, 100, 502, 504, 506, 507; 436/43, 436/45, 174, 180, 177, 179
See application file for complete search history.

(56) References Cited

U.S. PATENT DOCUMENTS

| | | |
|---|---|---|
| 5,242,606 A | 9/1993 | Braynin et al. |
| 5,256,376 A | 10/1993 | Callan et al. |
| 5,472,603 A | 12/1995 | Schembri |
| 5,693,233 A | 12/1997 | Schembri |
| 6,030,581 A | 2/2000 | Virtanen |
| 6,143,248 A | 11/2000 | Kellogg et al. |
| 6,302,134 B1 | 10/2001 | Kellogg et al. |
| 6,399,361 B2 | 6/2002 | Brotherston et al. |
| 6,488,896 B2 * | 12/2002 | Weigl et al. ............. 422/101 |
| 6,527,432 B2 | 3/2003 | Kellogg et al. |
| 6,548,788 B2 | 4/2003 | Kellogg et al. |
| 6,615,856 B2 * | 9/2003 | McNeely et al. ........... 137/14 |
| 6,632,399 B1 | 10/2003 | Kellogg et al. |
| 6,709,869 B2 | 3/2004 | Mian et al. |
| 6,729,352 B2 * | 5/2004 | O'Connor et al. .......... 137/827 |
| 6,743,399 B1 * | 6/2004 | Weigl et al. ............. 422/102 |
| 6,811,752 B2 * | 11/2004 | Barbera-Guillem ........ 422/100 |
| 6,880,576 B2 * | 4/2005 | Karp et al. ............... 137/806 |
| 2004/0096358 A1 * | 5/2004 | Blankenstein et al. ........ 422/58 |

* cited by examiner

*Primary Examiner* — Jill Warden
*Assistant Examiner* — Dwayne K Handy

(57) ABSTRACT

A microfluidic device comprises a microfluidic coupon and a fluid reservoir associated with the microfluidic coupon. The fluid reservoir has a vented configuration and a non-vented configuration, and is configured to contain a liquid to be centrifugated. An opening is formed in the fluid reservoir. When the microfluidic coupon is rotated at a target rotational velocity: the opening is open to flow of the liquid when the fluid reservoir is in the vented configuration; and the opening is closed to flow of the liquid when the fluid reservoir is in the non-vented configuration.

18 Claims, 3 Drawing Sheets

MICROFLUIDIC CENTRIFUGATION SYSTEMS

FIELD OF THE INVENTION

The present invention relates generally to systems for centrifugating microfluids.

BACKGROUND OF THE INVENTION

The use of microfluidic systems for the acquisition of chemical and biological information is becoming increasingly more important due to a number of considerations. For example, complicated biochemical reactions, when conducted in microfluidic volumes, may be carried out using very small volumes of liquid. As the volume of a particular liquid needed for such testing regimes is small, often on the order of nanoliters, the amounts of reagents and analytes used can be greatly reduced. Reduction in the amounts of reagents and analytes can greatly reduce the costs associated with microfluidic testing compared with conventional testing systems.

In addition, the response time of reactions is often much faster in microfluidic systems, leading to a decrease in the overall time required for a particular testing regime. Also, when volatile or hazardous materials are used or generated during testing, performing reactions in microfluidic volumes can increase the safety of a testing regime and can also reduce the quantities of hazardous materials that require specialized disposal after testing is completed.

In addition, microfluidic testing systems generally require much less bulky equipment than conventional testing systems, enabling use of microfluidic testing systems in mobile or residential settings. Microfluidic testing systems can thus be used in settings that conventionally required the sampling of fluids at one location and testing of the fluids at another location.

While microfluidic testing is increasing in popularity, the technology associated with microfluidic testing remains problematic in a number of areas. In particular, it has been found that sample preparation of various bodily fluids has been difficult to accomplish on a microfluidic level. For example, the analysis of blood often requires the removal of erythrocytes (red blood cells) for accurate testing. This has generally been accomplished by centrifugating a blood sample to separate the red blood cells from the remainder of the blood sample. Similar separation techniques have also been necessary to test saliva samples.

The small-scale nature of microfluidic testing systems has to date proved problematic when dealing with test samples that must be centrifugated prior to testing, with no known microfluidic centrifugation systems having been successfully developed. Due to this limitation in conventional microfluidic systems, centrifugation of samples to be tested has generally been accomplished with conventional, full-scale centrifugation devices after which a small (e.g., microfluidic) volume of the sample to be tested has been transferred to a microfluidic test coupon for further manipulation and analysis.

Accordingly, while it is desired to use microfluidic test systems in a wide range of applications, the limitations inherent in centrifugating liquids at the microfluidic level remain problematic.

SUMMARY OF THE INVENTION

It has been recognized that it would be advantageous to develop a system for effectively centrifugating liquids at the microfluidic level. The present invention provides a microfluidic device, including a microfluidic coupon and a fluid reservoir associated with the microfluidic coupon. The fluid reservoir can have a vented configuration and a non-vented configuration, and can be configured to contain a liquid to be centrifugated. An opening can be formed in the fluid reservoir. When the microfluidic coupon is rotated at a target rotational velocity: the opening is open to flow of the liquid when the fluid reservoir is in the vented configuration; and the opening is closed to flow of the liquid when the fluid reservoir is in the non-vented configuration.

In accordance with another embodiment of the invention, a method of microfluidically centrifugating and transporting a liquid is provided, including the steps of: disposing a liquid within a fluid reservoir associated with a microfluidic coupon, the fluid reservoir including an opening formed therein; rotating the microfluidic coupon at or above a target rotational velocity to centrifugate the liquid while substantially retaining the liquid within the fluid reservoir; venting the fluid reservoir; and rotating the microfluidic coupon at or above the target rotational velocity to centripetally drive the liquid through the opening.

In still another embodiment, a microfluidic device can comprise a microfluidic coupon, an array of fluid reservoir associated with the microfluidic coupon, and an opening formed in each of the fluid reservoirs. Each reservoir of the array of fluid reservoirs can each have a vented configuration and a non-vented configuration provided by a common master vent, and can further be configured to contain a liquid. When the microfluidic coupon is rotated at a target rotational velocity, each opening is open to flow of the liquid when the common master vent is in the vented configuration, and each opening is closed to flow of the liquid when the common master vent is in the non-vented configuration.

In yet another embodiment, a method of forming a microfluidic test coupon is provided, including the steps of: disposing a liquid within a fluid reservoir associated with a microfluidic coupon, the fluid reservoir having an opening formed therein; and creating a non-vented configuration in the fluid reservoir in a manner that allows an operator to create a vented configuration in the reservoir at a later time, such that when the microfluidic coupon is rotated at a target rotational velocity: the opening is open to flow of the liquid when the fluid reservoir is in the vented configuration; and the opening is closed to flow of the liquid when the fluid reservoir is in the non-vented configuration.

Additional features and advantages of the invention will be apparent from the detailed description which follows, taken in conjunction with the accompanying drawings, which together illustrate, by way of example, features of the invention.

DETAILED DESCRIPTION OF THE PREFERRED EMBODIMENT(S)

Figure 1:
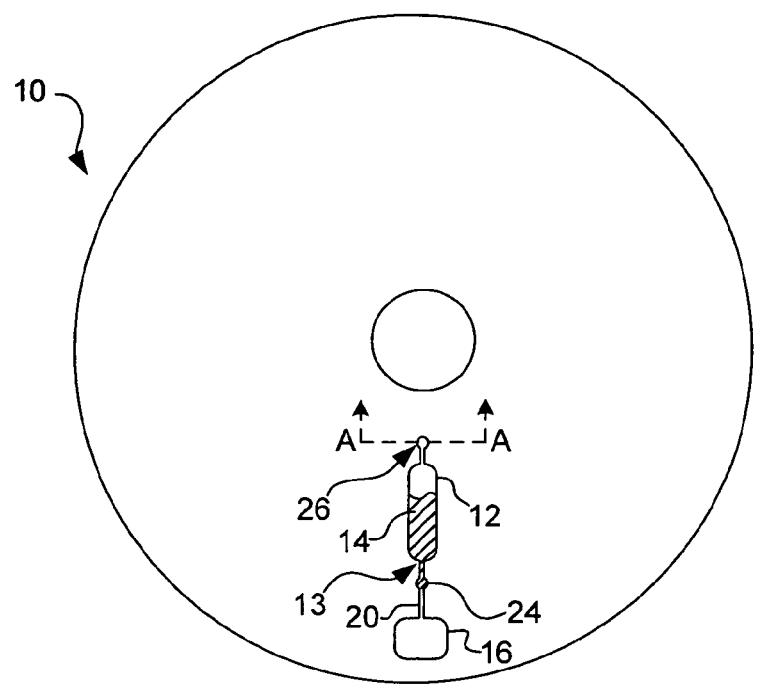
FIG. 1 is a schematic, top view of a microfluidic centrifugation coupon in accordance with an embodiment of the present invention.

Before particular embodiments of the present invention are disclosed and described, it is to be understood that this invention is not limited to the particular process and materials disclosed herein as such may vary to some degree. It is also to be understood that the terminology used herein is used for the purpose of describing particular embodiments only and is not intended to be limiting, as the scope of the present invention will be defined only by the appended claims and equivalents thereof.

In describing and claiming the present invention, the following terminology will be used:

The singular forms "a," "an," and "the" include plural referents unless the context clearly dictates otherwise.

As used herein, the terms "microfluidic coupon" or "coupon" are to be understood to refer to a device used to centrifugate and/or manipulate one or more microfluids, generally for the purposes of testing the fluid or liquid in a centrifugation test regime. Microfluidic coupons utilized in the present invention can include, but are not limited to, disk-shaped devices formed of poly(methylmethacrylate) (PMMA), acetonitrile-butadiene-styrene (ABS), polycarbonate, etc. While not so limited, such disks can be similar in appearance to well-known compact disks (CDs).

As used herein, the term "passive valve" is to be understood to refer to a static valve with no moving parts that acts as a fluid valve due primarily to its geometric configuration and/or size.

As used herein, the term "capillary valve" is to be understood to refer to a passive valve presenting a junction between two or more capillary channels and/or reservoirs that have at least one dimension less than about 1 mm.

As used herein, the term "microfluidics" and "microfluid" are to be understood to refer to fluids manipulated in systems that confine the fluids within geometric channels, passages, or reservoirs having at least one dimension less than about 1 mm. Similarly, the terms "microfluidic channel," or "microchannel" are to be understood to refer to channels having at least one dimension less than about 1 mm.

As used herein, the term "centrifugate," and its related terms "centrifugation" and "centrifugated," are to be understood to refer to a process in which a liquid is subjected to centripetal forces induced by rotating a reservoir in which the liquid is stored. While the term centrifugate is generally used to refer to a process in which two or more constituents of a liquid are separated due to centripetal force, the use of the term herein is not limited to any particular degree of separation of constituents of the liquid. Thus, a liquid can be centrifugated even when it has not yet exhibited visible separation of liquid constituents.

When referring to fluids such as "liquids," it is understood that not all constituents of the liquid are necessarily in liquid form. For example, blood is considered to be a liquid, even though it has solid cell constituents suspended therein. Liquid emulsions and microemulsions are also considered liquids, even though multiple liquids are present.

It is to be understood that the various features shown in the attached figures are for the purposes of illustration and do not in any manner limit the present invention. In particular, various fluids are represented in the figures by hatch markings. The hatch markings used to indicate the presence of a fluid are not to be construed to limit the invention to any particular type of fluid or material, even in the case where the hatch markings used may correspond to hatch markings used by those in various fields of endeavor to indicate a specific fluid or material.

The various microchannels and reservoirs utilized in the present centrifugation coupons can be formed in the coupon in a variety of manners. In one embodiment, these features can be machined in a surface of a disk using conventional milling techniques. After milling, a covering, such as a thin polymer film, can be applied over each channel and/or reservoir to enclose the respective channel and/or reservoir. In addition to this method, it is contemplated that the geometric features of the test coupons can be formed in a variety of manners known to those having ordinary skill in the art.

In addition, the relative levels of fluids in various reservoirs are shown schematically herein to aid in understanding of the invention, and may not provide an accurate indication of an actual amount of fluid or liquid contained within a reservoir or channel. Also, it is to be understood that liquids contained within channels, reservoirs or chambers can be forced toward one side or another of the channel, reservoir, or chamber, depending upon the net forces acting on the fluid body due to gravity, centripetal force, etc. Therefore, the fact that a body of fluid is shown in the figures as having an "upper" surface oriented in any particular direction may not correspond to the actual orientation of a fluid in a channel, reservoir, or chamber.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

The present invention provides systems for effectively centrifugating liquids on a microfluidic level that can be adapted for use with a variety of testing regimes. Examples of testing regimes that can benefit from the present invention include microfluidic biological, enzymatic, immunological, and chemical assay regimes. It is thought desirable to perform such testing on a microfluidic level for several reasons. Among other reasons, such systems generally utilize volumes of testing fluids well below those used in conventional systems, leading to advantages in decreased costs, more rapid reaction times, and minimized production and/or use of biohazardous materials.

Figure 2:
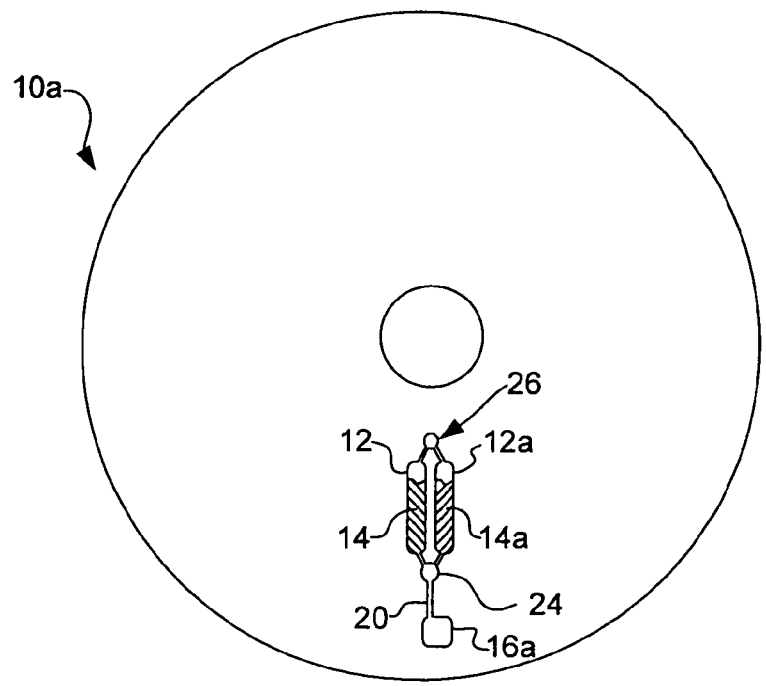
FIG. 2 is a schematic, top view of another microfluidic centrifugation coupon in accordance with an embodiment of the present invention.

Exemplary configurations of microfluidic centrifugation and/or fluid transport coupon or device in accordance with the present invention are shown generally at 10 and 10a in FIGS. 1 and 2. Referring specifically to FIG. 1, the microfluidic coupon can include a fluid reservoir 12 associated therewith. The fluid reservoir can be configured to contain a liquid 14 to be centrifugated. An opening 13 can be formed in the reservoir. An optional microchannel 20 can be fluidly connected to the fluid reservoir, which can be positioned downstream from the fluid reservoir.

A vent 26 can be formed as part of, or can be fluidly connected to, the fluid reservoir 12. In either case, it can be said that the walls of the vent at least partially define the fluid reservoir. In other words, the fluid reservoir can be defined to include a large area where a bulk of the liquid 14 is stored, as well as any microchannels and/or vent regions that may be present. Thus, the fluid reservoir includes the general region where the liquid is stored or centrifugated prior to opening the vent. The vent can be operable to selectively provide a vented atmosphere "behind" the fluid reservoir; e.g., a vented atmosphere radially inward of the direction in which the fluid will travel when subject to centrifugal forces induced by rotating the coupon 10. The opening 13 can be open to flow of the liquid from the fluid reservoir, and thus through the microchannel 20, when the coupon is rotated at or above a target rotational velocity (discussed in more detail below). Thus, in this aspect of the invention, the opening is open to flow of the fluid from the reservoir when the coupon is rotated at or above the target rotational velocity, and when the reservoir or vent is in a vented configuration.

Also shown in the figures is optional passive valve 24 that can serve to replace or enhance the opening 13 to control flow of the liquid 14 from the fluid reservoir 12. The passive, capillary valves of the present invention are based on the use of rotationally-induced fluid pressure which, when exceeding a particular pressure, is sufficient to overcome capillary forces which tend to prevent liquids from flowing. Liquids which completely or partially wet internal surfaces of microchannels which contain them experience a resistance to flow when moving from a microchannel of narrow cross section to one of larger cross section. Conversely, liquids that do not wet these surfaces resist flowing from microchannels of large cross section to those with smaller cross section. The capillary pressure can vary according to the sizes of the two microchannels in question, the surface tension of the fluid, and the contact angle of the fluid on the material of the microchannels. Accordingly, as used herein, a target rotational velocity of a coupon is one that produces sufficient centripetal force to generate a pressure in a liquid body that is high enough to overcome capillary forces in a particular capillary valve to enable the liquid to flow through the capillary valve. Further, the velocity at which fluid flow can occur can be reduced by venting the fluid reservoir in accordance with embodiments of the present invention.

The size of microchannels utilized in the present invention is generally less than about 1 mm, and often as small as about 500 µm or less, along at least one dimension or even all dimensions. By varying capillary valve cross sectional dimensions as well as the position and extent along the radial direction of the fluid flow components of the present centrifugation coupons, capillary valves are developed which release fluid flow in a rotation-dependent manner. Capillary valves similar to those utilized herein are discussed in detail in publications such as U.S. Pat. No. 6,143,248.

It will be appreciated by those having ordinary skill in the art that conventional capillary valves similar to those discussed above generally operate in a system in which liquids are free to flow through various microchannels and test chambers on a coupon in which back pressure, e.g., pressure radially inward of the direction of travel of a liquid through a microfluidic path, is non-restrictive of movement. Thus, liquids controlled by conventional capillary valves are generally subject only to centripetal forces and capillary forces, and need not overcome negative back pressures to travel through a microfluidic path formed on a coupon.

In one embodiment of the invention, opening 13 and passive valve 24 can be used in series, as shown in FIG. 1, in which case the opening will generally be sized large enough such that flow from the reservoir 12 is controlled by the smaller, more restrictive passive valve. In this case, the passive valve is open to flow of the liquid 14 from the reservoir when the coupon 10 is rotated at or above the target rotational velocity, and the vent 26 is properly configured to allow appropriate venting. As used herein, the term "open to flow of liquid" is to be understood to refer to a condition in which the capillary valve or opening, when sufficiently vented through vent fluidly coupled to or part of the fluid reservoir, will allow the liquid to flow through the capillary valve, and optionally, into microchannel 20 if present. However, in those embodiments in which the vent is selectively closed (or not opened; e.g., non-vented), the closed vent restricts flow of the liquid through the opening or capillary valve, even in the case where the coupon is rotated at or above the target rotational velocity. In this manner, the present invention allows the liquid to be centrifugated at rotational velocities greater than the target rotational velocity without being released by the passive valve. In this configuration, the passive valve can be said to be "closed to flow," even though the opening or passive valve is configured as an open channel, in that the liquid cannot pass through the valve or opening until the reservoir is properly vented.

In contrast, in conventional microfluidic systems utilizing conventional capillary valving, the liquid 14 would be released by the opening or capillary valve at the point in time when the rotational velocity of the coupon 10 reached or exceeded the target rotational velocity. Due to this limitation, conventional microfluidic systems, if used to centrifugate liquids, would be limited to centrifugating the liquids at rotational speeds below the target rotational velocity. These lower rotational velocities have been found generally not effective to separate the liquid into distinct constituents. This is due to the fact that the liquid being centrifugated can be released through the capillary valve before the coupon reaches a rotational rate necessary to separate the constituents of the liquid, or before the liquid was rotated for a period of time sufficient to separate the constituents of the liquid.

The present invention addresses this problem by providing vent 26 that can be selectively opened to provide at least two configurations to the fluid reservoir 12. When the vent is closed, the fluid reservoir can have a non-vented configuration in which the liquid 14 is restricted from flowing through the opening 13 or the passive valve 24, even when the coupon is rotated at or above the target velocity. When the vent is opened, the fluid reservoir can have a vented configuration in which the liquid is not restricted from flowing through the opening or the passive valve and will flow through the opening or passive valve when the coupon is rotated at or above the target rotational velocity. In this manner, the liquid can be centrifugated at rotational rates equal to or greater than the target rotational rate without passing from the fluid reservoir through the opening or the passive valve. Centrifugation at or above the target rotational velocity can be performed as desired until the vented configuration is created in the reservoir, after which the liquid will pass through the opening or the passive valve when the coupon is rotated at or above the target rotational velocity.

In operation, the present invention provides a method of microfluidically centrifugating and transporting a liquid 14, including the step of disposing the liquid within fluid reservoir 12 associated with the microfluidic coupon 10. The microfluidic coupon can then be rotated at or above the target rotational velocity to centrifuge the liquid while substantially retaining the liquid within the fluid reservoir. After centrifugation, the fluid reservoir can be vented at which point the microfluidic coupon can be rotated at or above the target rotational velocity to centripetally drive the liquid through the opening or the passive valve.

In the embodiments shown in the figures, the reservoir 12 is fluidly connected to vent 26 which is utilized to create the vented or non-vented configuration in the reservoir. It other embodiments of the invention, however, the reservoir itself can be provided with a covering which can be vented or non-vented, as the case may be, without requiring the presence of a vent. For simplicity of discussion herein, however, vent 26 is utilized to provide the vented or non-vented configuration to the reservoir, with the understanding that the function of vent 26 can be integrated into the structure of reservoir 12. Thus, in some embodiments of the invention, the fluid reservoir 12 can itself function as the vent and can have a pierceable membrane or openable seal (discussed in more detail below) that can provide the vented and non-vented configurations.

The vented and non-vented configurations of the reservoir 12 can be created in a number of manners. In one embodiment of the invention, shown by example in cross section in FIG. 3A, a pierceable membrane 23 can define at least a portion of the vent 26 (and thus the fluid reservoir 12) when the membrane is in an uncompromised (e.g., intact) condition. By piercing the member with, for example, piercing tool 32, a vented configuration can be created in the vent, and thus in the reservoir. The pierceable membrane can be formed from a variety of materials, and in one embodiment is formed of transparent packing tape that can be applied over the reservoir (and/or the vent) after the liquid has been deposited in the reservoir. The piercing tool 32 can be of a variety of known tools, including, in one embodiment, a syringe that can be wielded by a test technician to create the vented configuration at the appropriate time.

Figure 3A:
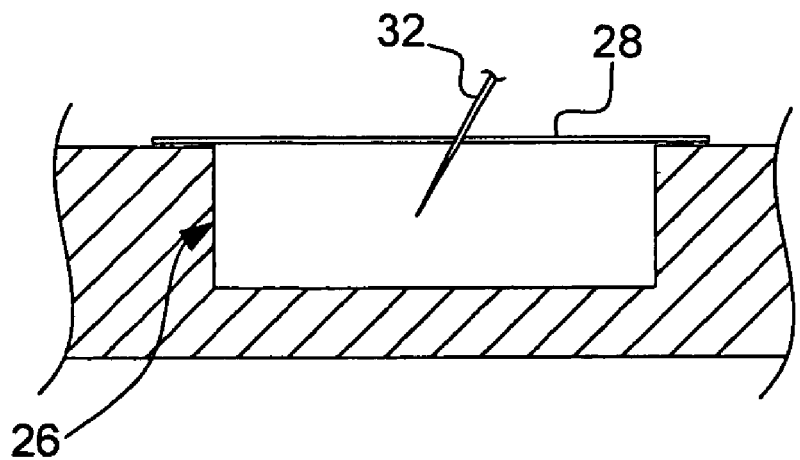
FIG. 3A is a cross sectional view of a section of the microfluidic centrifugation coupon of FIG. 1, taken along section A-A of FIG. 1.
Figure 3B:
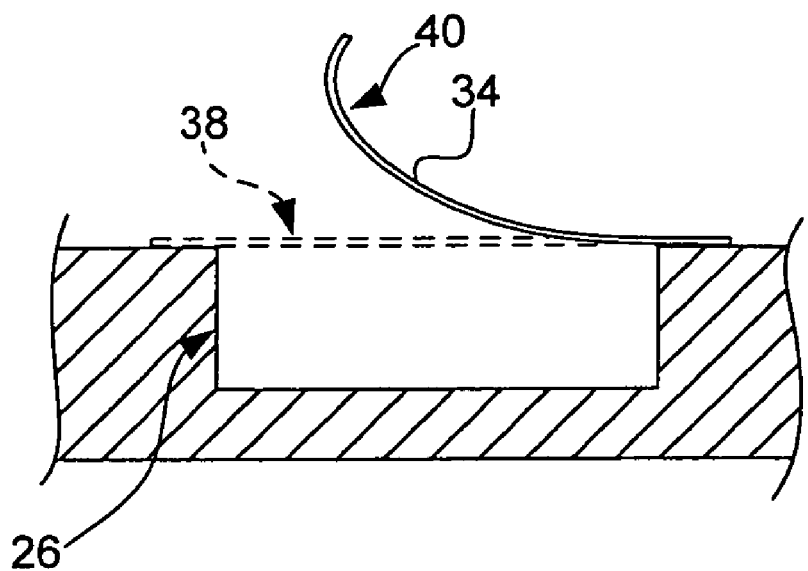
FIG. 3B is a cross sectional view of another embodiment of the section of the microfluidic centrifugation coupon of FIG. 1 taken along section A-A of FIG. 1.

In the embodiment of the invention shown by example in FIG. 3B, an openable seal 34 can be adhered over, or to, the vent 26 (or to the reservoir 12) to provide the non-vented configuration in the fluid reservoir when in a closed condition (shown by example in position 38). The vented configuration in the reservoir can be created by opening (shown by example in position 40) the seal 34. While the openable seal can take a variety of forms, in one aspect of the invention the openable seal comprises a peelable layer removably adhered to the reservoir. In this manner, the peelable layer can provide the non-vented configuration to the fluid reservoir when substantially fully adhered to the reservoir or vent (e.g., in position 38) and can provide the vented configuration to the reservoir when at least partially peeled from the reservoir or vent (e.g., in position 40).

The pierceable membrane 28 of FIG. 3A and the openable seal 34 of FIG. 3B shown in the figures are generally configured to be manipulated by a test technician to create the vented configuration in the reservoir 12 after a suitable degree of centrifugation of the liquid 14 has been achieved. In addition to these manual techniques, however, it is contemplated that the present invention can incorporate automatic manipulation devices which can create the vented configuration in the reservoir without requiring action by the technician. For example, it is contemplated that the rotation device or system (not shown) used to rotate the centrifugation coupon can include a piercing component that can pierce the pierceable membrane at a predetermined time or at a predetermined level of separation of the liquid.

In the exemplary embodiment illustrated in FIG. 1, the centrifugation coupon 10 includes a single fluid reservoir 12 fluidly coupled to a test chamber 16 via microchannel 20. In this embodiment, the liquid 14 is held within the reservoir 12 by the opening 13 or the passive valve 24 until a desired degree of centrifugation of the liquid has been achieved. At this point, the vented configuration can be established in the reservoir 12 and the coupon can be rotated at a rate sufficient to force the liquid beyond the opening or the valve, through the microchannel, and into the test chamber. The liquid can be mixed with one or more reactants (not shown) that can be present within the test chamber. The reactants can facilitate testing of at least one constituent of the liquid. A variety of reactants can be utilized in testing the liquid, including liquid reactants and dry reactants, as would occur to one having ordinary skill in the art.

In the embodiment shown in FIG. 2, the coupon 10a can include two fluid reservoirs, 12 and 12a, which can each contain a liquid, 14 and 14a, respectively. In this aspect of the invention, either or both of the liquids can be centrifugated, then released to travel into test chamber 16a, where either or both of the liquids can be tested. While the invention is not so limited, liquid 14a can be a reactant with which it is desired to mix liquid 14 to test liquid 14 according to a particular testing regime.

It is noted that the embodiments illustrated in the figures are for exemplary purposes only, and that the various reservoirs, microchannels, and test chambers of the present invention can be arrayed on the centrifugation coupon in a variety of manners. For example, in the configuration shown in FIG. 1, liquid 14 can be separated into at least two constituent materials (not shown) due to centrifugation of the liquid. It may be the case that one of these constituents (generally the more dense constituent) will become concentrated in the reservoir near the outlet to passive valve 24. Thus, when the vented configuration is created in reservoir 12, this latter constituent would likely enter the test chamber 16 prior to, or to the exclusion of, the other constituent.

Figure 4A:
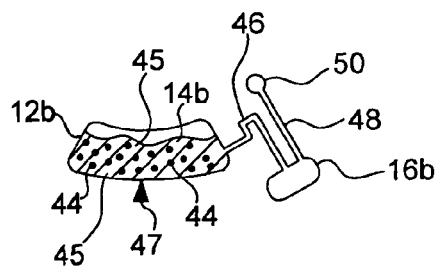
FIG. 4A is a schematic, top view of a portion of a microfluidic centrifugation coupon in accordance with an embodiment of the present invention in an pre-centrifugated state.
Figure 4B:
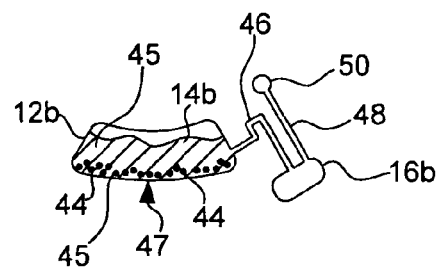
FIG. 4B is a schematic, top view of the portion of the microfluidic centrifugation coupon of FIG. 4A in a centrifugated state.

If it were desired to direct the less dense constituent contained in the reservoir to the test chamber 16 after centrifugation, the outlet path from the reservoir to the test chamber can be routed differently, to allow the less dense constituent to exit the reservoir and enter the test chamber, either prior to, or to the exclusion of, the more dense constituent. This embodiment is illustrated in FIGS. 4A and 4B. In the embodiment of FIG. 4A, which is shown prior to centrifugation of a disk (not shown) with which fluid reservoir 12b is associated, liquid 14b includes at least two constituents, particulates 44 and less dense liquid 45. As shown in FIG. 4B, after centrifugation of the liquid, the heavier particulates settle toward the radially outward wall 47 of the reservoir, leaving the less dense liquid in the radially inward portion of the reservoir. In this manner, the less dense liquid can be routed through microchannel 46 and into testing chamber 16b. Vent line 48 and vent port 50 can be provided to facilitate flow of the less dense liquid through microchannel and into the testing chamber.

While it is anticipated that the present invention can be utilized in a variety of testing regimes, no specific testing regime is detailed herein, as it is believed that those of ordinary skill in the art can readily incorporate the present invention into a variety of testing regimes. In particular, it is contemplated that the present invention can be advantageously incorporated into testing regimes that utilize multiple fluid reservoirs, testing chambers, microchannels, reagents, etc., to perform multiple stages of tests, various flow sequencing events, etc., as would occur to one having ordinary skill in the art. In this manner, it is contemplated that the present invention can be particularly effective in performing testing requiring or benefiting from flow sequencing events which move fluids between different sections of the test coupon at different time intervals.

Figure 5:
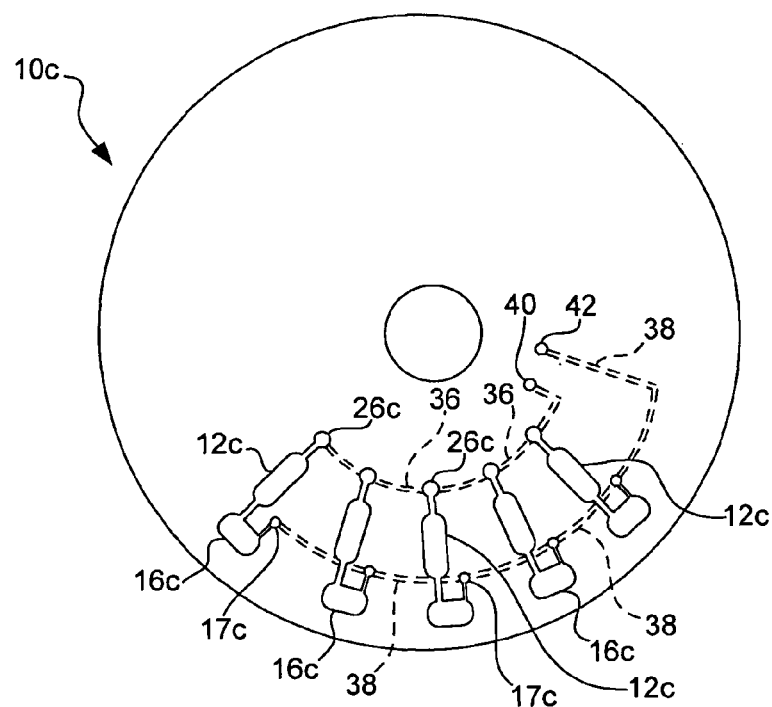
FIG. 5 a schematic, top view of a microfluidic centrifugation coupon in accordance with another embodiment of the present invention.

Furthermore, while each fluid reservoir is shown in the figures as having a dedicated vent, it is contemplated that multiple reservoirs can share a common vent that, when ruptured or otherwise vented, creates a vented condition in each of the multiple reservoirs causing fluid contained in each reservoir to flow from the reservoir. One example of such a configuration is shown at 10c in FIG. 5. In this embodiment, a series of fluid reservoirs 12c can each be coupled to a series of testing chambers 16c. Each of the fluid reservoirs can include a vent 26c that can be coupled to each of the other vents 26c via a central vent line 36. The central vent line 36 can be coupled to master vent 40 that, when punctured or otherwise vented, provides the vented configuration to each of the fluid reservoirs 12c. Similarly, each testing chamber 16c can include a downstream vent 17c that is coupled to each of the other downstream vents via central vent line 38. Central vent line 38 can be coupled to master vent 42 that, when punctured or otherwise vented, provides a vented configuration to each of the downstream vents. In this manner, control of fluid (not shown) between each fluid reservoir and its associated testing chamber can be controlled via one or both of master vents 40 and 42, and/or any of the other vents that are more individually associated with each fluid reservoir. Of course, the present invention can also provide multiple fluid reservoirs that can each be vented at different times to motivate fluid flow from each of the multiple reservoirs at a different time.

The mechanism used to rotate or spin the centrifugation coupons of the present invention is not shown in the figures; it being understood that those having ordinary skill in the art can devise numerous rotational devices capable of rotating the present centrifugation coupons at rotational velocities suitable for the present methods.

It is to be understood that the above-referenced arrangements are illustrative of the application for the principles of the present invention. Numerous modifications and alternative arrangements can be devised without departing from the spirit and scope of the present invention while the present invention has been shown in the drawings and described above in connection with the exemplary embodiments(s) of the invention. It will be apparent to those of ordinary skill in the art that numerous modifications can be made without departing from the principles and concepts of the invention as set forth in the claims.

What is claimed is:

1. A microfluidic device, comprising:
(a) a microfluidic coupon configured to hold a liquid within a fluid reservoir while the liquid is rotated at a target rotational velocity such that a predetermined degree of centrifugation of the liquid is achieved prior to allowing the liquid to exit therefrom;
(b) the fluid reservoir defined by the microfluidic coupon, the fluid reservoir being fluidically connected through a microchannel to a vent located radially inward from the microchannel in the microfluidic coupon, the fluid reservoir being in a non-vented configuration by the vent including a peelable layer or pierceable membrane at an entrance from the vent into the microchannel, or the fluid reservoir being in a vented configuration by the peelable layer or pierceable membrane being peeled or pierced; and the fluid reservoir further being configured to contain the liquid; and
(c) an exit opening formed in the fluid reservoir fluidically connected to the vent through the fluid reservoir and the microchannel, and located radially outward on the fluid reservoir in the microfluidic coupon;

wherein, when the microfluidic coupon is rotated at the target rotational velocity:
(i) the exit opening allows flow of the liquid only when the fluid reservoir is in the vented configuration; and
(ii) the exit opening does not allow flow of the liquid when the fluid reservoir is in the non-vented configuration.

2. The device of claim 1, further comprising a passive valve, wherein the microchannel is fluidly connecting the fluid reservoir and the passive valve, and wherein:
the passive valve allows flow of the liquid when the fluid reservoir is in the vented configuration; and
the passive valve does not allow flow of the liquid when the fluid reservoir is in the non-vented configuration.

3. The device of claim 1, further comprising a piercing tool configured to pierce the pierceable membrane to provide the vented configuration to the fluid reservoir.

4. The device of claim 1, wherein the peelable layer is removably adhered to the fluid reservoir, the peelable layer providing:
the non-vented configuration to the fluid reservoir when adhered to the fluid reservoir; and
the vented configuration to the fluid reservoir when at least partially peeled from the fluid reservoir.

5. The device of claim 2, wherein the passive valve comprises a capillary valve, the capillary valve being always open to the atmosphere, but allowing fluid flow into the capillary valve when the fluid reservoir is in the vented configuration and the microfluidic coupon has reached the target rotational velocity.

6. The device of claim 1, further comprising a test chamber in fluid communication with the fluid reservoir, the test chamber containing a reactant with which at least one constituent of the liquid is to be mixed to test the liquid.

7. The device of claim 1, wherein the liquid includes constituents that can be separated by centrifugation.

8. The device of claim 7, wherein the target rotational velocity is such that the liquid becomes separated when the opening is closed to fluid flow.

9. The device of claim 7, wherein when the microfluidic coupon travels at the target rotational velocity and the reservoir is in the vented configuration, the liquid is transported through the exit opening.

10. The device of claim 1 wherein when the vent is closed, the closed vent is configured to restrict the liquid from flowing through the exit opening when the coupon is rotated above the target rotational velocity.

11. A microfluidic device, comprising:
(a) a microfluidic coupon configured to hold a liquid within an array of fluid reservoirs while the liquid is rotated at a target rotational velocity such that a predetermined degree of centrifugation of the liquid is achieved prior to allowing the liquid to exit therefrom;
(b) the array of fluid reservoirs defined by the microfluidic coupon, each reservoir of the array of fluid reservoirs being fluidically connected through a microchannel to a vent located radially inward from the microchannel in the microfluidic coupon, and each vent being coupled to other vents of the array of fluid reservoirs by a central vent line, the central vent line being connected to a common master vent, the common master vent being initially closed by including a peelable layer or pierceable membrane at an entrance from the common master vent into the central vent line, or the common master vent being open by the peelable seal or pierceable membrane of the common master vent being peeled or pierced; and each reservoir being configured to contain the liquid; and (c) an exit opening formed in each of the fluid reservoirs fluidically connected to each vent through each of the respective fluid reservoirs and microchannels, and located radially outward on each of the respective fluid reservoirs in the microfluidic coupon;

wherein, when the microfluidic coupon is rotated at the target rotational velocity:

(i) each exit opening allows flow of the liquid only when the common master vent is open; and (ii) each exit opening does not allow flow of the liquid when the common master vent is closed.

12. A method of microfluidically centrifugating and transporting a liquid, comprising the steps of:

(a) disposing a liquid within a fluid reservoir associated with a microfluidic coupon, the fluid reservoir being defined by the microfluidic coupon and being fluidically connected through a microchannel to a vent located radially inward from the microchannel in the microfluidic coupon, the fluid reservoir being in a non-vented configuration by the vent including a peelable layer or a pierceable membrane at an entrance from the vent into the microchannel, the fluid reservoir having formed therein an exit opening i) fluidically connected to the vent through the fluid reservoir and the microchannel, and ii) located radially outward on the fluid reservoir in the microfluidic coupon;

(b) rotating the microfluidic coupon at or above a target rotational velocity to centrifugate the liquid while substantially retaining the liquid within the fluid reservoir, wherein the microfluidic coupon is configured to hold the liquid within the fluid reservoir while the liquid is rotated at the target rotational velocity such that a predetermined degree of centrifugation of the liquid is achieved prior to allowing the liquid to exit therefrom, the exit opening not allowing flow of the liquid at the target rotational velocity while the fluid reservoir is in the non-vented configuration;

(c) venting the fluid reservoir by peeling or piercing the peelable layer or the pierceable membrane, whereby the fluid reservoir is in a vented configuration; and (d) rotating the microfluidic coupon at or above the target rotational velocity to centripetally drive the liquid through the opening, wherein when the microfluidic coupon is rotated at the target rotational velocity and the fluid reservoir is in the vented configuration, the exit opening allows flow of the liquid.

13. The method of claim 12, wherein the microfluidic coupon further includes a passive valve, wherein the microchannel is fluidly connecting the fluid reservoir to the passive valve, and wherein:

the passive valve allows flow of the liquid when the fluid reservoir is in the vented configuration; and the passive valve does not allow flow of the liquid when the fluid reservoir is in the non-vented configuration.

14. The method of claim 12, wherein the peelable layer is removably adhered to the fluid reservoir, and wherein the step of venting the fluid reservoir includes the step of at least partially peeling the peelable layer from the fluid reservoir.

15. The method of claim 13, wherein the passive valve comprises a capillary valve.

16. The method of claim 12, wherein the microfluidic coupon includes a test chamber in fluid communication with the fluid reservoir, the test chamber containing a reactant with which the liquid is to be mixed to test the liquid.

17. The method of claim 12, wherein the step of rotating the microfluidic coupon to centrifugate the liquid includes the step of rotating the microfluidic coupon until the liquid is separated into at least two constituent liquids or phases.

18. A method of forming a microfluidic test coupon, comprising the steps of:

(a) disposing a liquid within a fluid reservoir associated with a microfluidic coupon, the fluid reservoir being defined by the microfluidic coupon and being fluidically connected through a microchannel to a vent located radially inward from the microchannel in the microfluidic coupon, the fluid reservoir being in a non-vented configuration by the vent including a peelable layer or a pierceable membrane at an entrance from the vent into the microchannel, or being in a vented configuration by the peelable layer or pierceable membrane being peeled or pierced, the fluid reservoir having formed therein an exit opening i) fluidically connected to the vent through the fluid reservoir and the microchannel, and ii) located radially outward on the fluid reservoir in the microfluidic coupon; and (b) providing the non-vented configuration in the fluid reservoir in a manner that allows an operator to create the vented configuration in the reservoir at a later time, the microfluidic fluid being configured to hold the liquid within the fluid reservoir while the liquid is rotated at the target rotational velocity such that a predetermined degree of centrifugation of the liquid is achieved prior to allowing the liquid to exit therefrom, such that when the microfluidic coupon is rotated at a target rotational velocity:

(i) the exit opening only allows flow of the liquid when the fluid reservoir is in the vented configuration; and (ii) the exit opening does not allow flow of the liquid when the fluid reservoir is in the non-vented configuration.

\* \* \* \* \*